(12) United States Patent
Cherukuri

(10) Patent No.: US 8,202,538 B2
(45) Date of Patent: Jun. 19, 2012

(54) ORALLY DISINTEGRATING LAYERED COMPOSITIONS

(75) Inventor: Subraman Rao Cherukuri, Vienna, VA (US)

(73) Assignee: Capricorn Pharma, Inc., Frederick, MD (US)

( * ) Notice: Subject to any disclaimer, the term of this patent is extended or adjusted under 35 U.S.C. 154(b) by 281 days.

(21) Appl. No.: 11/819,326

(22) Filed: Jun. 26, 2007

(65) Prior Publication Data

US 2008/0014268 A1   Jan. 17, 2008

Related U.S. Application Data

(60) Provisional application No. 60/805,834, filed on Jun. 26, 2006.

(51) Int. Cl.
  *A61K 9/24* (2006.01)
  *A61K 9/00* (2006.01)
  *A61K 9/22* (2006.01)
  *A61K 9/28* (2006.01)

(52) U.S. Cl. ......... 424/472; 424/400; 424/468; 424/474

(58) Field of Classification Search .................. 424/472, 424/400, 468, 474
   See application file for complete search history.

(56) References Cited

U.S. PATENT DOCUMENTS

| | | | |
|---|---|---|---|
| 4,686,212 A * | 8/1987 | Ducatman et al. | 514/161 |
| 4,832,956 A | 5/1989 | Gergely et al. | |
| 5,204,116 A * | 4/1993 | Edgren et al. | 424/473 |
| 5,686,109 A | 11/1997 | Fujitsu et al. | |
| 5,912,012 A | 6/1999 | Carlin et al. | |
| 6,375,982 B1 | 4/2002 | Cherukuri | |
| 6,406,717 B2 | 6/2002 | Cherukuri | |
| 6,419,954 B1 | 7/2002 | Chu et al. | |
| 6,589,556 B2 | 7/2003 | Cherukuri | |
| 6,645,988 B2 | 11/2003 | Phillips | |
| 7,229,641 B2 | 6/2007 | Cherukuri | |
| 2002/0168404 A1 * | 11/2002 | Rault et al. | 424/468 |
| 2004/0220276 A1 | 11/2004 | Cousin et al. | |
| 2004/0247677 A1 | 12/2004 | Oury et al. | |
| 2005/0196438 A1 * | 9/2005 | Wang et al. | 424/464 |
| 2008/0020065 A1 | 1/2008 | Cherukuri | |

FOREIGN PATENT DOCUMENTS

| | | |
|---|---|---|
| EP | 1 279 402 B1 | 11/2006 |
| WO | WO 00/51568 | 9/2000 |
| WO | WO 03/017985 | 3/2003 |

OTHER PUBLICATIONS

Material Safety Data Sheet, Magnesium stearate, Science Lab.com, Oct. 10, 2005, pp. 1-6.*
Notification of Transmittal of the International Search Report and the Written Opinion of the International Searching Authority, or the Declaration, dated Aug. 8, 2008.

* cited by examiner

*Primary Examiner* — Robert A Wax
*Assistant Examiner* — Aradhana Sasan
(74) *Attorney, Agent, or Firm* — Hunton & Williams LLP

(57) ABSTRACT

The present invention is directed to multi-layered compositions for oral administration having at least one orally disintegrating layer and capable of maintaining layer cohesion. The present invention is also directed to methods of manufacturing such compositions.

27 Claims, No Drawings

ORALLY DISINTEGRATING LAYERED COMPOSITIONS

This application claims the benefit of U.S. Provisional Patent Application Ser. No. 60/805,834 filed Jun. 26, 2006, which is herein incorporated by reference in its entirety.

FIELD OF THE INVENTION

The present invention relates to oral dosage tablets for administering one or more active agents, and methods for the production and use of such. Accordingly, this invention involves the fields of chemistry, pharmaceutical sciences, medicine, and other health sciences.

BACKGROUND OF THE INVENTION

Orally disintegrating mono-layer tablets are known in the art and widely accepted today in several therapeutic categories. However, there are several practical limitations to these mono-layer orally disintegrating tablets in their manufacturing and storage/handling aspects. For example, these tablets in general are soft and need to be blister-packaged directly off the tablet press. Alternatively, the tablets need to be compressed at very low compression forces, which cannot be used with tablets prepared by direct compression or wet granulation. Additionally, for those orally disintegrating mono-layer tablets containing a coated active, it is important to compress at the lowest force possible, so the coating will not be ruptured under compression. These compression and disintegration issues are further complicated if the orally disintegrating tablet comprises two or more layers where at least one layer is an orally disintegrating layer. One solution may be to use a melt granulation process which allegedly may permit using a compression force as low as 2 kN; direct compression formulations, on the other hand, require compression forces greater than 5 kN.

While such a solution may be acceptable for a monolayer orally disintegrating tablet, such a low compression would not permit a multi-layered tablet having at least one orally disintegrating layer. In the case of a multi-layer tablet, it is imperative that the multiple layers remain attached to each other throughout the shelf-life and use in commerce and that the layers do not separate. Typically, to maintain cohesion of the multiple layers, the tablet must be compressed using a higher force than the force used to compress a monolayer orally disintegrating tablet. Increased compression force results in increased tablet hardness, which, in turn, results in delayed and/or slowed disintegration to unacceptably longer times, i.e., longer than 60 seconds. For example, tablets with hardness greater than 1 kP may not be orally disintegrating, i.e., they may take 1 minute or more to dissolve in the mouth of a subject.

There is a need for a multi-layered tablet that has at least one orally disintegrating layer and that is capable of maintaining layer cohesion throughout storage, transport, and handling.

BRIEF SUMMARY OF THE INVENTION

The present invention is directed to multi-layered compositions for oral administration having at least one orally disintegrating layer and capable of maintaining layer cohesion. The present invention is also directed to methods of manufacturing such compositions.

DETAILED DESCRIPTION OF THE INVENTION

The present invention is directed to multi-layered compositions and methods of manufacturing them.

Definitions

In describing and claiming the present invention, the following terminology will be used in accordance with the definitions set forth below.

The singular forms "a," "an," and "the" include plural referents unless the context clearly dictates otherwise. Thus, for example, reference to "a drug" includes reference to one or more of such drugs, and reference to "an excipient" includes reference to one or more of such excipients.

As used herein, the terms "formulation" and "composition" each refer to a mixture of two or more compounds, elements, or molecules. For example, in some aspects, the terms "formulation" and "composition" may be used to refer to a mixture of one or more active agents with a carrier or other excipients. The term "formulation" usually refers to a mixture of components prior to constituting a dosage form. The term "composition" usually refers to a mixture of components that may be administered as a dosage form.

As used herein, the term "active agent" refers to a substance that has measurable specified or selected physiologic and/or pharmacologic activity when administered to a subject. Active agents include, but are not limited to, drugs, including prodrugs, and dietary supplements. These terms of art are well-known in the pharmaceutical and medicinal arts.

As used herein, a "therapeutically effective amount" refers to a non-toxic amount that is sufficient to achieve therapeutic effects: to treat, cure, prevent, mitigate, or relieve the symptoms or underlying cause of a disease or condition. A "therapeutically effective amount" may depend on various biological factors, which may affect the ability of a substance to perform its intended task and should be taken into consideration. The achievement of therapeutic effects may be measured by a physician or other qualified medical personnel using evaluations known in the art; it is recognized that individual variation and response to treatments may make the achievement of therapeutic effects a somewhat subjective decision. The determination of a therapeutically effective amount is well within the ordinary skill in the art of pharmaceutical sciences and medicine. See, e.g., Meiner and Tonascia, "Clinical Trials: Design, Conduct, and Analysis," *Monographs in Epidemiology and Biostatistics*, Vol. 8 (1986), incorporated herein by reference.

As used herein, "subject" refers to a mammal including, but not limited to, human patients, domestic animals, livestock, and clinical test animals. Exemplary subjects include, but are not limited to, humans, mice, rats, horses, pigs, cattle, dogs, cats, rabbits, and aquatic mammals. In one embodiment, the subject may benefit from the administration of a composition of this invention.

As used herein, the term "carrier" refers to any inert and pharmaceutically acceptable material that has substantially no biological activity and that can be used as a substantial component of a formulation.

The term "admixed" means that the active agent and/or other ingredients are dissolved, dispersed, or suspended in the carrier. In some cases, the active agent may be uniformly admixed in the carrier.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. The term "about" means a particular value can have a range acceptable to those of skill in the art given the nature of the value and the method by which it is determined. For example, the term "about" can mean within 50% of a given value, preferably with 20%, more preferably within 10%, and most preferably within 5%.

As used herein, the term "substantially intact" means that the composition retains its size and shape without dividing into physically separate fragments, each fragment encompassing more than 25% of the composition. Ideally, "substantially intact" means that the layers remain attached along the entire original attachment surfaces.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed as a range. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, this numerical range includes individual values of varying precision such as 1, 2, 2.8, 3, 3.5, 4, and 5, and sub-ranges, such as 1-3, 2.7-4, and 3-5, etc. This same principle applies to ranges reciting only one numerical value as a minimum or a maximum. Furthermore, such an interpretation should apply regardless of the breadth of the range or the characteristics being described.

As used herein, the term "layer" refers to a homogeneous region within a heterogeneous composition. A "monolayer" composition is simply homogeneous throughout, whereas a multi-layered composition has a plurality of homogeneous regions, wherein at least two of the homogeneous regions are not identical to one another. Each layer can be of various and independent size and shape.

Adjacent layers may contact one another at a planar or non-planar surface of contact. Each layer may have a surface area along the planar or non-planar surface of contact that is the same as or different from the surface area of other layers along the same surface of contact. The surface area of a layer that touches an adjacent layer is the attachment surface. The attachment surface of a layer to an adjacent layer may be of any size. Thus, layers can be aligned, shifted, wholly or partially overlapped, or partially surrounded respective to one another.

A layer can be formed by applying pressure or energy to a mass of materials that may be present as a solid or semi-solid powder, granules, particles, or a mixture thereof. For example, solid powder or granules may be compressed under pressure in a tabletting machine to form a layer.

As used herein, the term "coating" refers to a formulation applied as a liquid or dispersion onto solid particles or a solid composition. A coating can be applied, for example, by spray drying. The coating can be applied to one or more surfaces, or it can wholly or partially surround the particles or composition.

Layered Compositions

In one embodiment, the present invention provides a composition for oral administration comprising at least two layers, wherein at least one layer comprises an active agent; at least one layer is capable of oral disintegration; and the composition comprises a means for maintaining layer cohesion. In another embodiment, the present invention provides a composition for oral administration comprising at least two layers, wherein at least one layer comprises an active agent; at least one layer is capable of oral disintegration in less than 45 seconds; and the composition remains substantially intact upon friability testing.

The composition comprises at least two layers, preferably two or three layers. Each layer can comprise zero, one, or more than one active agent. In one embodiment, the composition comprises a bilayer tablet wherein each of the two layers comprises an active agent. For example, one layer can contain aspirin, while another layer contains a statin.

In another embodiment, the composition comprises a trilayer tablet, wherein a first and second layer each comprise an active agent, and a third layer, preferably disposed between the other two layers, does not comprise an active agent. This type of third layer, which does not contain an active agent, can be called a barrier layer. A barrier layer (or a barrier coating, see below) can be useful to separate layers containing incompatible active or inactive ingredients. The incompatibility may be, for example, a physical incompatibility that may result in discoloration or instability of the product, or a chemical incompatibility that may lead to degradation or decomposition of one of the active agents.

The active agent(s) in each layer can be the same as or different from the active agent(s) in another layer with respect to identity, concentration, amount, release profile, and/or format (e.g., presence or absence of coatings). The disintegration characteristics of the layer formulation (e.g., whether the layer is orally disintegrating or not) may be selected independently of the characteristics of the active agent contained therein (e.g., identity, concentration, amount, release profile, and/or format). For example, immediate release aspirin can be contained in an orally disintegrating layer or in a non-orally disintegrating layer. Likewise, modified release aspirin can be contained in an orally disintegrating or a non-orally disintegrating layer.

The means for maintaining layer cohesion is any component or structural feature that contributes to maintaining a substantially intact composition. For a multi-layered tablet composition, the means for maintaining layer cohesion contributes to maintaining tablet integrity such that each of layers remains attached to one another during friability testing, storage, transport, and/or handling. In a preferred embodiment, each layer comprises at least one means for maintaining layer cohesion.

In one embodiment, the means for maintaining layer cohesion comprises one or more bonding agents. A bonding agent can be any component that melts in response to compression forces, resulting in increased interlayer and/or intralayer cohesion. In particular, the compression force is sufficient to make the bonding agent reach its glass transition temperature (Tg) such that the bonding agent becomes liquid. Exemplary bonding agents include, but are not limited to, polyethylene glycol (PEG) 8000, polyethylene glycol esters (preferably water insoluble PEG esters), and lipid materials. PEG 8000 is a preferred bonding agent.

When the bonding agent is a lipid material, the lipid material is preferably a fat or wax having a melting point of about 25° C. to about 90° C., preferably about 35° C. to about 40° C., and most preferably about 37° C. Exemplary lipid materials include, but are not limited to, cocoa butter, hydrogenated tallow, hydrogenated vegetable oil, hydrogenated cotton seed oil, hydrogenated palm kernel oil, soybean oil, stannol ester, and derivatives thereof. Preferred lipid materials include hydrogenated vegetable oil, hydrogenated palm kernel oil, cocoa butter, and derivatives thereof. In one embodiment, the bonding agent is cocoa butter. Other polar lipid materials may also be capable of melting upon compression and thus acting as bonding agents, e.g., surfactants, especially those having a hydrophilic-lipophilic balance (HLB) lower than 8.

The bonding agent is present in a layer formulation in an amount of about 0.01% to about 70%, about 0.01% to about 50%, about 0.01% to about 5%, or about 0.01% to about 3% by weight of the layer. In one embodiment, the bonding agent is PEG present in an amount of 0.01% to about 5% by weight of the layer.

The composition preferably remains substantially intact upon friability testing. See, e.g., the European or U.S. Pharmacopeia standard friability tests. Friability testing can be performed according to USP 29, <1216>. Ten whole tablets are tested. Tablets are weighed before testing. Then, the friabilator drum is allowed to complete 100 revolutions. Whole tablets are collected and weighed. Percentage loss is determined from initial weight. The normal limit for USP friability is not more than 1% loss.

The composition comprises at least one layer capable of oral disintegration, i.e., capable of rapid oral disintegration in saliva with no need for chewing or drinking liquids to ingest. In one embodiment, one layer can be capable of oral disintegration, while another layer is intended to be chewed, swallowed, and/or retained in the mouth for a prolonged time (longer than the orally disintegrating layer, e.g., one minute or longer). Alternatively, each of the layers can be capable of oral disintegration. An orally disintegrating layer completely disintegrates in saliva and/or in an in vitro medium in less than 60 seconds, preferably less than 50, 45, 40, 35, 30, 25, 20, 15, or 10 seconds. In one embodiment, disintegration time is 10 to 30 seconds (e.g., 10, 12, 14, 16, 18, 20, 22, 24, 26, 28 or 30 seconds). Disintegration time depends on the size and surface area of the layer as well as the amount and type of insoluble ingredients, e.g., coated active.

The composition can further comprise a means for increasing disintegration. In a preferred embodiment, each layer that is capable of oral disintegration comprises at least one means for increasing disintegration. The means for increasing disintegration increases the rate or extent of disintegration of the composition in saliva and/or in an in vitro medium. The means for increasing disintegration can be one or more super-disintegrants or salivating agents.

Disintegrants facilitate disintegration of the composition into smaller pieces or particles, which dissolve more rapidly. Disintegrants include, but are not limited to, water soluble PEGs, polyols (e.g., xylitol) in powder format, starch, sodium starch glycolate, alginates, microcrystalline cellulose, gums, guar gums, gum karaya, gellan gum, chitin, and chitosan. Super-disintegrants are associated with high dissolution rates and can be used in low amounts, typically about 1% to about 20%, about 1% to about 18%, or about 1% to about 15% by weight of the formulation. Super-disintegrants typically exhibit a high swelling volume and hydration capacity. Exemplary super-disintegrants include, but are not limited to, crosslinked cellulose (e.g., crosscarmelose, Ac-Di-Sol®), crosslinked polymer (e.g., crospovidone, Polyplasdone XL-10®, Kollidon), crosslinked starch (e.g., sodium starch glycolate, Primojel®), and resin complexes (e.g., divinyl benzene, polystyrene).

Salivating agents include, but are not limited to, super-emulsifiers and food acids. Super-emulsifiers typically exhibit a hydrophilic-lipophilic balance (HLB) greater than 8, preferably about 8 to about 40, about 8 to about 20, about 15 to about 40, or about 20 to about 45. Super-emulsifiers include, but are not limited to, alkyl aryl sulfonates, alkyl sulfates, sulfonated amides and amines, sulfated and sulfonated esters and ethers, alkyl sulfonates, polyethoxylated esters, mono- and diglycerides, diacetyl tartaric esters of monoglycerides, polyglycerol esters, sorbitan esters and ethoxylates, lactylated esters, phospholipids, lecithin, polyoxyethylene sorbitan esters, propylene glycol esters, and sucrose esters. Food acids include, but are not limited to, citric acid, malic acid, tartarate, food salts, sodium chloride, salt substitutes, and potassium chloride. The salivating agent is preferably present in an amount of about 0.05% to about 15%, about 0.05% to about 5%, about 0.1% to about 1%, or about 0.3% to about 0.4% by weight of the formulation.

The compositions of the present invention may further comprise one or more coatings, including, but not limited to, an enteric coating, a barrier coating, a cosmetic coating, a protective coating, or a finishing coating. Note that a barrier coating differs from a barrier layer in that a coating is applied as a liquid or dispersion whereas a layer is formed from a solid or semi-solid. Cosmetic coatings, protective coatings, and finishing coatings do not significantly affect the release characteristics of an active agent. A coating can be applied to the entire or partial surface area of a particle, a layer, or a composition as a whole. In one embodiment, at least one layer is coated with a barrier coating so as to cover at least the attachment surface to an adjacent layer.

For example, a protective coating may comprise up to about 15% by weight of the layer or of the composition. The protective coating can be applied using any conventional coating formulation and will include one or more film-formers or binders, hydrophilic polymers (e.g., hydroxypropylmethyl cellulose (HPMC)), and hydrophobic polymers (e.g., ethyl cellulose, cellulose acetate, polyvinyl alcohol-maleic anhydride copolymers, acrylic copolymers, beta-pinene polymers, glyceryl esters of wood resins), and plasticizers (e.g., polyethylene glycol, triethyl citrate, diethyl phthalate, propylene glycol, glycerin, butyl phthalate, and castor oil).

The film formers are applied from a solvent system containing one or more solvents including water; alcohols such as methyl alcohol, ethyl alcohol, or isopropyl alcohol; ketones such as acetone or ethylmethyl ketone; and chlorinated hydrocarbons such as methylene chloride, dichloroethane, and 1,1,1-trichloroethane.

The layers can the same as or different from one another with respect to weight, size, shape, and/or color. In one embodiment, the layers can be distinguished by color.

Active agent particles can comprise granules, microparticles, and/or nanoparticles. The active agent particles can be coated with one or more of a taste-masking agent, a release-modifying agent, an enteric coating, a protective coating and/or a finishing coating according to methods known in the art. Active agents can be coated as pure agents or after spheronization or agglomeration. The particles for coating can, but need not be spherical. The particles can be rod-shaped or irregular. Coated active agents can reduce side effects and can reduce incompatibility among active agents. For example, the composition can comprise enteric-coated aspirin. The enteric-coated aspirin granules can be further coated with a protective coating or a finishing coating. If side effects and/or incompatibility are not problematic, e.g., at low dosages, the active agent can be uncoated.

Conventional enteric polymer coatings in aqueous or non-aqueous systems include, for example, Eudragit L-30D-55 (acrylic acid copolymers-Rohm Pharma) (5 to 25% solids) containing 10 to 15% of diethylphthalate (w/w) as plasticizer in an aqueous system. Other exemplary enteric polymer coatings include Eudragit R and S series resins (acrylic acid copolymers-Rohm Pharma), cellulose acetate phthalate, cellulose acetate maleate, cellulose acetate succinate, hydroxypropylmethyl cellulose phthalate, hydroxypropylmethyl cellulose acetate succinate, and a suitable plasticizer such as triethyl citrate, diethyl phthalate, tributyl citrate, triacetin, dibutyl phthalate, dibutyl sebicate, Myvacet 940, or any other commonly used plasticizers suitable for use with enteric polymers. Any polymer with any suitable plasticizer can be used in an aqueous or non-aqueous system to form an enteric coating on the active agent granule or particle, on a layer, or on the composition.

Each layer formulation preferably comprises granules, which preferably have a particle size of about 700 µm to about 1 µm. In one specific aspect, one layer comprises more granules than the other layer on a weight/weight ratio. For example, one layer may comprise from about 100% to about 500% of granules compared to the other layer. In one aspect, the range may be about 110% to about 400%; about 110% to about 300%; or about 110% to about 200% by weight/weight.

The layer formulation can comprise nanoparticles or microparticles, which can be used as-is or further granulated. The nanoparticles and microparticles preferably have a particle size of about 10 to about 2000 nm. Nanoparticles can be prepared by a variety of processes known in the art including, but not limited to, micronization, coacervation, co-precipitation methods. Processes for preparing microparticles are similarly well known.

A layer formulation may further comprise inactive ingredients that affect the pharmacological, pharmacokinetic, and/or pharmacodynamic properties of the active agent. Such ingredients can be called "pharmacokinetic or pharmacodynamic modifiers." Pharmacokinetic or pharmacodynamic modifiers include, but are not limited to, absorption modifiers, oral cavity residence time modifiers, pH altering agents, solubility altering agents, viscosity altering agents, chelating agents, sequestering agents, and microsuspension or microemulsion formers.

A pH altering agent alters the pH of the microenvironment of the active agent thereby reducing or increasing the solubility of the active ingredient in the saliva, which affects subsequent absorption from the oral, buccal, and/or gastrointestinal cavity. Exemplary pH altering agents include both alkalinizing agents and acidifiers. An alkalinizing agent increases the pH of the microenvironment, preferably to a pH of 7.0 or higher. Exemplary alkalinizing agents include, but are not limited to, alkali or alkali earth metal salts, sodium or potassium or calcium or zinc salts of bicarbonates, carbonates, citrates, etc. An acidifying agent decreases the pH of the microenvironment, preferably to a pH of 7.0 or lower. Exemplary acidifying agents include, but are not limited to, weak salts of mineral acids such as ammonium sulfate, bismuth phosphate, etc.

A viscosity altering agent alters the viscosity of the microenvironment, e.g., in the oral cavity, thereby altering the residence time of the active agent in the microenvironment and affecting absorption of the active agent. Exemplary viscosity altering agents include, but are not limited to, cellulosic materials including hydroxypropylmethyl cellulose (HPMC), methylcellulose, sodium carboxymethyl cellulose and hydroxypropyl cellulose; alginates; gums including guar gum, xanthan gum, locust bean gum, gum acacia, gum Arabic; carrageenan; pectin; and modified starch.

In a preferred embodiment, the composition has a hardness of about 2 kP to about 9 kP, preferably about 5 kP to about 7 kP or about 4 kP to about 6 kP (kiloponds) (1 kilopond=0.00980665 kilonewton). Hardness is a term used in the art to describe the diametral breaking strength as measured by conventional pharmaceutical hardness testing equipment, such as a Schleuniger Hardness Tester.

In a preferred embodiment, the composition is a tablet, i.e., a small, essentially solid pellet of any shape. Tablet shapes maybe cylindrical, spherical, rectangular, capsular, oval, oblong, or irregular. Various tablet sizes can be prepared, e.g., about 2 to 2000 mg in total weight. Tablets can be scored to provide for fractional doses.

The compositions described herein may advantageously provide fast disintegration, good mouth feel, and/or physical stability.

Active Agents

The compositions of the invention can comprise any active agent that can be orally administered to a subject. Any amount of an active agent that does not significantly affect or negate beneficial tablet features, such as disintegration, hardness, friability, and mouth feel are within the scope of the invention.

In a preferred embodiment, the active agent is included in the composition in a therapeutically effective amount. One of ordinary skill can determine appropriate amounts to achieve a therapeutic effect. The dose can be adjusted according to age, weight, and condition of the patient, as well as the route of administration, dosage form, regimen, and the desired result. Dose amounts can be monitored, escalated, and/or adjusted according to the expertise of the clinician. The compositions can be administered in single or divided doses of one to four times daily.

For example, a statin can be included in amounts of about 0.1 mg to 2000 mg per day in single or divided doses, preferably about 0.2 mg to about 200 mg per day. Suggested daily dosages are known in the art: 10-40 mg pravastatin, 10-80 mg lovastatin, 5-40 mg simvastatin, 10-80 mg atorvastatin, 20-80 mg fluvastatin, and 0.2-0.3 mg cerivastatin.

The active agent can be prepared to achieve a variety of release profiles including immediate release or modified release including, but not limited to, delayed release, sustained release, zero-order release, delayed-and-sustained release, and pulsatile release. The release profile can be selected independently of the layer formulation's disintegration characteristics. That is, a layer formulation can be designed to orally disintegrate, but contain active agent particles designed for modified release after swallowing. Alternatively, the orally disintegrating layer can contain an active agent for immediate release.

The active agent can be absorbed via any route of oral administration including oral, buccal, sublingual, mucosal, and/or upper or lower gastrointestinal absorption. The mechanism of absorption can be selected independently of the layer formulation's disintegration characteristics.

Exemplary active agents include, but are not limited to:

1) antipyretic analgesic anti-inflammatory agents such as indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone, or etodolac;

2) antiulcer agents such as ranitidine, sulpiride, cetraxate hydrochloride, gefarnate, irsogladine maleate, cimetidine, lanitidine hydrochloride, famotidine, nizatidine, or roxatidine acetate hydrochloride;

3) coronary vasodilators such as nifedipine, isosorbide dinitrate, diltiazem hydrochloride, trapidil, dipyridamole, dilazep dihydrochloride, methyl 2,6-dimethyl-4-(2-nitrophenyl)-5-(2-oxo-1,3,2-dioxaphosphorinan-2-yl)-1,4-dihydropyridine-3-carboxylate, verapamil, nicardipine, nicardipine hydrochloride, or verapamil hydrochloride;

4) peripheral vasodilators such as ifenprodil tartrate, cinepazide maleate, cyclandelate, cinnarizine, or pentoxyfyline;

5) oral antibacterial and antifungal agents such as penicillin, ampicillin, amoxicillin, cefalexin, erythromycin ethylsuccinate, bacampicillin hydrochloride, minocycline hydrochloride, chloramphenicol, tetracycline, erythromycin, fluconazole, itraconazole, ketoconazole, miconazole, or terbinafine;

6) synthetic antibacterial agents such as nalidixic acid, piromidic acid, pipemidic acid trihydrate, enoxacin, cinoxacin, ofloxacin, norfloxacin, ciprofloxacin hydrochloride, or sulfamethoxazole trimethoprim;

7) antispasmodics such as popantheline bromide, atropine sulfate, oxapium bromide, timepidium bromide, butylscopolamine bromide, rospium chloride, butropium bromide, N-methylscopolamine methylsulfate, or methyloctatropine bromidebutropium bromide;

8) antitussive, anti-asthmatic agents such as theophylline, aminophylline, methylephedrine hydrochloride, procaterol hydrochloride, trimetoquinol hydrochloride, codeine phosphate, sodium cromoglicate, tranilast, dextromethorphane hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, calbetapentane citrate, oxeladin tannate, or isoaminile citrate;

9) bronchodilators such as diprophylline, salbutamol sulfate, clorprenaline hydrochloride, formoterol fumarate, orciprenalin sulfate, pirbuterol hydrochloride, hexoprenaline sulfate, bitolterol mesylate, clenbuterol hydrochloride, terbutaline sulfate, mabuterol hydrochloride, fenoterol hydrobromide, or methoxyphenamine hydrochloride;

10) diuretics such as furosemide, acetazolarmide, trichlormethiazide, methyclothiazide, hydrochlorothiazide, hydroflumethiazide, ethiazide, cyclopenthiazide, spironolactone, triamterene, fluorothiazide, piretanide, metruside, ethacrynic acid, azosemide, or clofenamide;

11) muscle relaxants such as chlorphenesin carbamate, tolperisone hydrochloride, eperisone hydrochloride, tizanidine hydrochloride, mephenesin, chlorozoxazone, phenprobamate, methocarbamol, chlormezanone, pridinol mesylate, afloqualone, baclofen, or dantrolene sodium;

12) brain metabolism altering drugs such as meclofenoxate hydrochloride;

13) minor tranquilizers such as oxazolam, diazepam, clotiazepam, medazepam, temazepam, fludiazepam, meprobamate, nitrazepam, or chlordiazepoxide;

14) major tranquilizers such as sulpiride, clocapramine hydrochloride, zotepine, chlorpromazinon, or haloperidol;

15) beta-blockers such as pindolol, propranolol hydrochloride, carteolol hydrochloride, metoprolol tartrate, labetalol hydrochloride, acebutolol hydrochloride, butetolol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride, or bupranolol hydrochloride;

16) antiarrhythmic agents such as procainamide hydrochloride, disopyramide, ajimaline, quinidine sulfate, aprindine hydrochloride, propafenone hydrochloride, or mexiletine hydrochloride;

17) gout suppressants allopurinol, probenecid, colchicine, sulfinpyrazone, benzbromarone, or bucolome;

18) anticoagulants such as ticlopidine hydrochloride, dicumarol, or warfarin potassium;

19) antiepileptic agents such as phenytoin, sodium valproate, metharbital, or carbamazepine;

20) antihistamines such as brompheniramine maleate, chlorpheniramine maleate, cremastin fumarate, mequitazine, alimemazine tartrate, or cycloheptazine hydrochloride;

21) antiemetics such as difenidol hydrochloride, metoclopramide, domperidone, betahistine mesylate, or trimebutine maleate;

22) hypotensives such as dimethylaminoethyl reserpilinate dihydrochloride, rescinnamine, methyldopa, prazosin hydrochloride, bunazosin hydrochloride, clonidine hydrochloride, budralazine, or urapidin;

23) sympathomimetic agents such as dihydroergotamine mesylate, isoproterenol hydrochloride, or etilefrine hydrochloride;

24) expectorants such as bromhexine hydrochloride, carbocysteine, ethyl cysteine hydrochloride, or methyl cysteine hydrochloride;

25) oral antidiabetic agents such as glibenclamide, tolbutamide, or glymidine sodium;

26) circulatory agents such as ubidecarenone or ATP-2Na;

27) iron preparations such as ferrous sulfate or dried ferrous sulfate;

28) vitamins such as vitamin B1, vitamin B2, vitamin B6, vitamin B12, vitamin C, vitamin A, vitamin D, vitamin E, vitamin K or folic acid;

29) pollakiuria remedies such as flavoxate hydrochloride, oxybutynin hydrochloride, terodiline hydrochloride, or 4-diethylamino-1,1-dimethyl-2-butynyl (I)-alpha-cyclohexyl-alpha-phenylglycolate hydrochloride monohydrate;

30) angiotensin-converting enzyme inhibitors such as enalapril maleate, alacepril, or delapril hydrochloride;

31) anti-viral agents such as trisodium phosphonoformate, didanosine, dideoxycytidine, azido-deoxythymidine, didehydro-deoxythymidine, adefovir dipivoxil, abacavir, amprenavir, delavirdine, efavirenz, indinavir, lamivudine, nelfinavir, nevirapine, ritonavir, saquinavir, or stavudine;

32) high potency analgesics such as codeine, dihydrocodeine, hydrocodone, morphine, dilandid, demoral, fentanyl, pentazocine, oxycodone, pentazocine, or propoxyphene;

33) antihistamines such as brompheniramine maleate;

34) nasal decongestants such as phenylephrine HCl, phenylpropanolamine HCl, or pseudoephedrine; and 35) cholesterol-lowering agents such as statins, including pravastatin, atorvastatin, simvastatin, lovastatin, cerivastatin, or fluvastatin;

36) vitamins, minerals, and dietary supplements such as ascorbic acid or zinc.

A layer can contain one active agent, or it can contain a mixture or combination of two or more active agents. Mixtures of active agents can include active agents of the same category (e.g., two nasal decongestants), active ingredients from two different categories (e.g., an antihistamine and a nasal decongestant), or a combination thereof (two nasal decongestants and an antihistamine). The active agents in the foregoing list may provide alternative therapeutic effects instead or in addition to the therapeutic effect described above.

Inactive Ingredients

In preferred embodiments, each layer formulation contains one or more excipients. Any pharmaceutically acceptable excipient known in the art can be included in a layer formulation, such as binders, diluents or bulking agents, disintegrants, glidants, lubricants, anti-adherents, silica flow conditioners, emulsifiers, surfactants, flavors, colorants, souring agents, sweeteners, preservatives, stabilizers, antioxidants, and antibacterial agents.

Binders include, but are not limited to, corn starch, pregelatinized starch, polyvinyl pyrrolidone (PVP), hydroxypropylmethyl cellulose (HPMC), ethyl cellulose, cellulose acetate, gum tragacanth, acacia, and gelatin. The binder is typically present in an amount of about 0.5% to about 20%, preferably about 1% to about 10% by weight of the formulation.

Bulking agents include, but are not limited to, lactose, microcrystalline cellulose, wood cellulose, corn starch, modified corn starch, calcium phosphate, sugar, dextrose, mannitol or sorbitol. The bulking agent is typically present in an amount of about 1% to about 90%, preferably about 5% to about 85% by weight of the formulation.

Suitable disintegrants include, but are not limited to, corn starch, potato starch, alginic acid, and sodium starch glycolate.

Glidants and lubricants may facilitate removing the composition from a die without sticking. These include, but are not limited to, silicon dioxide (e.g., Syloid), castor oil, hydrogenated vegetable oils and fats, magnesium stearate, zinc stearate, calcium stearate, talc, carnauba wax, stearic acid, palmitic acid. The glidant or lubricant is typically present in an amount of about 0.01% to about 4%, preferably about 0.02% to about 2% by weight of the formulation or independently added to the die.

Emulsifiers are known in the art and specifically include surfactants. Categories of suitable surfactants include, but are not limited to, hydrophilic surfactants, both ionic and nonionic, as well as lipophilic surfactants. Exemplary surfactants include, but are not limited to, Polyethoxylated fatty acids such as PEG 4-100 monolaurate, PEG-4 laurate, PEG-5 stearate;

PEG-fatty acid diesters such as PEG-4 dilaurate, PEG 400 DL, PEG 1000 DS;

PEG-fatty acid mono- and di-ester mixtures such as PEG 4-150 mono, dilaurate, PEG 200-6000 mono dilaurate, PEG 4-150 mono distearate;

Polyethylene glycol glycerol fatty acid esters such as PEG-20 glyceryl laurate, PEG-40 glyceryl laurate, PEG-30 glyceryl oleate;

Alcohol-oil transesterification products such as PEG 20 castor oil, PEG-100 hydrogenated castor oil, PEG-60 corn glycerides;

Polyglycerized fatty acids such as polyglyceryl-2 stearate, polyglyceryl-3 oleate, polyglyceryl-10 linoleate;

Propylene glycol fatty acid esters such as propylene glycol monocaprylate, propylene glycol monooleate, propylene glycol dioctanoate;

Mixtures of propylene glycol esters-glycerol esters;

Mono- and diglycerides such as monopalmitolein, 3-4 glyceryl monoleate, glyceryl monostearate;

Sterol and sterol derivatives such as sitosterol, phytosterol, soya sterol;

Polyethylene sorbitan fatty acid esters such as sorbitan laurate, sorbitan monolaurate, sorbitan monostearate;

Polyethylene glycol alkyl ethers such as PEG-10 oleyl ether, PEG-10 cetyl ether, PEG-10 stearyl ether;

Sugar esters such as sucrose distearate/monostearate, sucrose monostearate, sucrose monopalmitate;

Polyethylene glycol alkyl phenols such as PEG-10-100 nonyl phenol, PEG-15-100 octyl phenol ether;

Polyoxyethylene-polyoxypropylene block copolymers such as Poloxamer 105 a=11 b=16, Poloxamer 185 a=19 b=30, Poloxamer 338 a=128 b=54;

Sorbitan fatty acid esters such as sorbitan monooleate, sorbitan sesquioleate, sorbitan monoisostearate;

Lower alcohol fatty acid esters such as ethyl oleate, isopropyl myristate, isopropyl linoleate;

Ionic surfactants such as sodium oleate, sodium taurocholate, palmitoyl carnitine;

Unionized ionizable surfactants such as free fatty acids, bile acids; and

Derivatives of fat-soluble vitamins such as vitamins A, D, E, K.

The compositions can also include flavors (e.g., strawberry aroma, raspberry aroma, cherry flavor, key lime flavor, grape flavor trusil art 5-11815, orange, cherry, fruit extracts, magnasweet 135, prosweet, peppermint, or wintergreen), flavor enhancers, sweeteners (e.g., aspartame, saccharine, sorbitol, glucose, sucrose, lactose), souring agents (e.g., citric acid), dyes, and/or colorants. For example, the composition can be coated with sugar.

The compositions can also include one or more buffering agents. For example, a statin can be formulated with a buffering agent to prevent undesirable interaction with other active agents, e.g., aspirin. The buffering agent can be used to buffer the active agent to inhibit gastrointestinal side effects. Conventional acid buffers include, but are not limited to, calcium carbonate, magnesium oxide, magnesium carbonate, magnesium hydroxide, aluminum hydroxide, dihydroxyaluminum sodium carbonate, aluminum magnesium hydroxide sulfate, and aluminum hydroxide magnesium carbonate co-dried gel. The buffering agent is present in an amount sufficient to achieve the buffering effect, typically about 10 mg to about 1000 mg, preferably about 50 mg to about 500 mg, depending on the amount of active agent.

Antioxidants include, but are not limited to, vitamin E, vitamin C, folic acid, vitamin $B_6$, vitamin $B_{12}$, and sodium bisulfite.

Methods of Manufacture

In one embodiment, the present invention provides a method of preparing a layered composition as described above, the method comprising compressing at least two layers together to form a tablet at a pressure of about 17 to about 25 kN, preferably about 19 to about 23 kN, or about 21 kN. The compression pressure is high enough to ensure the formation of a tablet with acceptable hardness, but low enough to prevent chipping or fracture of the composition during routine packaging, shipping, and handling. In a preferred embodiment, the compression force is sufficient to melt the bonding agent and thereby promote layer cohesion. The method can further comprise one or more pre-compression steps, wherein the composition is compressed at pressure sufficient to remove air from the die, but insufficient to form a solid tablet. The pre-compression force is typically less than the compression force and is typically about 10 to about 20 kN, about 10 kN to about 15 kN, about 12 to about 14 kN, or about 14 kN.

In one embodiment, the method comprises: preparing a plurality of layer formulations, each layer formulation comprising a bonding agent; placing at least two layer formulations in direct or indirect contact with one another; and compressing the plurality of layer formulations together to form a layered tablet. The at least two layers are in direct contact with one another when they touch one another. The two layers are in indirect contact when the layers are compressed together, but are separated by an intervening layer or coating.

In one embodiment, the present invention provides a method of preparing a bilayer tablet comprising: preparing a first layer formulation comprising a first bonding agent; preparing a second layer formulation comprising a second bonding agent that is the same as or different from the first bonding agent; placing the first layer formulation in direct contact with the second layer formulation; and compressing the first layer formulation and the second layer formulation together to form a bilayer tablet.

In one embodiment, the present invention provides a method of preparing a layered composition comprising: preparing a plurality of layer formulations, applying a precompression force to a first layer formulation, optionally compressing the first layer formulation, placing a second layer formulation in direct or indirect contact with the first layer formulation; applying a precompression force to the first and second layers, and compressing the layer formulations together to form a layered tablet. Subsequent layers can be similarly constructed.

The methods can include one or more quality assurance tests, e.g., testing the rate of oral disintegration and/or testing the friability. In one embodiment, the method includes a step of confirming that the layered composition remains substantially intact upon friability testing.

The methods can further comprise a step of controlling speed flow of powder into a die. While gravity feed or force feed can be used, force feed is preferred. Controlling the speed flow facilitates the distribution of a flowing powder before compression. A typical force feeder consists of a force feeder chamber that houses two adjustable paddles, and an opening at the bottom which covers the die filling area. A hopper is connected to the feeder from the top. The paddles are rotated by an external drive, forcing the materials into the die cavity. Force feeding ensures consistent and uniform filling and avoids irregular filling, irregular hardness, and/or rate variation.

A layer formulation can be prepared by granulation according to a variety of processes known in the art. Examples include, but are not limited to, dry granulation, wet granulation, spray congealing, fluid bed granulation, and melt granulation. Melt granulation can be performed in a high shear mixer (e.g., Diosna), low shear mixer (e.g., tumbling bed mixers such as twin shell blenders or V-blender), or fluid bed granulator (e.g., Glatt and Aeromatic fluid bed granulators).

The granules may be milled and/or screened using any mills commonly used for milling tablet granulations such as, for example, CoMill, Stokes Oscillator, etc. In one embodiment, the granules are screened through a mesh sized 20-100.

Once layer formulations are prepared, they may be formed into various shapes. In preferred embodiments, the layer formulation(s) are pressed into a shape. This process may comprise placing the formulation(s) into a die and applying pressure to yield a composition having the shape of the surface of the die. Hydraulic presses such as a Carver Press or rotary tablet presses such as the Stokes Versa Press can be used to compress the compositions of the invention.

In a preferred embodiment, compression is applied to give a composition having a hardness of about 2 to about 9 kP, preferably about 5 to about 7 kP.

EXAMPLES

Example 1

Bilayer Tablet Comprising Ascorbic Acid and Zinc

Orally disintegrating tablets can be prepared comprising ascorbic acid and zinc salts in one layer, and zinc salts (i.e., without ascorbic acid) in another layer.

The first layer is white and comprises zinc salts as the active agent as well as excipients:

TABLE 1

Layer formulation comprising zinc salts

| Component | Amount (% weight/weight) |
|---|---|
| Zinc Acetate Dihydrate | 3.22 |
| Zinc Gluconate Dihydrate | 2.40 |
| Mannitol Granules | 59.60 |
| Microcrystalline Cellulose | 22.00 |
| Povidone USP | 0.73 |
| Polyplasdone ® Premix* | 7.70 |
| Sodium Lauryl Sulfate | 0.05 |
| Sorbitan Monostearate | 1.00 |
| Polyethylene Glycol 8000 | 1.00 |
| Magnesium Stearate | 0.6 |
| Talc USP | 0.2 |
| Silicon dioxide NF | 0.1 |
| Natural Orange Flavor | 1.0 |
| Sucralose NF | 0.40 |

*The Polyplasdone ® Premix comprises Polyplasdone XL-10 ® (51.948% w/w), sodium starch glycolate (44.676% w/w), and Tween 80 (3.376% w/w).

The materials were sifted individually through #24 Screen. The materials were then blended in a double cone blender, mixed for 20 minutes, and then mixed for another 10 minutes.

The second layer is colored and comprises active agents ascorbic acid and zinc salts as well as excipients:

TABLE 2

Layer formulation comprising ascorbic acid and zinc salts

| Component | Amount (% weight/weight) |
|---|---|
| Zinc Acetate Dihydrate | 3.22 |
| Zinc Gluconate Dihydrate | 2.40 |
| Encapsulated Ascorbic Acid 64.22% | 7.03 |
| Mannitol Granules | 52.32 |
| Microcrystalline Cellulose 90M | 22.00 |
| Povidone USP | 0.73 |
| Polyplasdone ® Premix | 7.70 |
| Sodium Lauryl Sulfate NF | 0.05 |
| Sorbitan Monostearate | 1.00 |
| Polyethylene Glycol 8000 Powder | 1.00 |
| Magnesium Stearate | 0.6 |
| Talc USP | 0.2 |
| Silicon dioxide | 0.1 |
| Natural Orange Flavor | 1.0 |

TABLE 2-continued

Layer formulation comprising ascorbic acid and zinc salts

| Component | Amount (% weight/weight) |
|---|---|
| Sucralose | 0.40 |
| Yellow # 6 Aluminum Lake | 0.25 |

The materials were sifted individually through #24 Screen. The materials were then blended in a double cone blender, mixed for 20 minutes, and then mixed for another 10 minutes.

Each layer formulation was fed to a hopper, placed into a die, then compressed to form an orally disintegrating bilayer tablet. In this composition, each layer is orally disintegrating and each layer comprises a different set of active agent(s) from the other layer. One of the active agents, ascorbic acid, is coated. In this embodiment, PEG 8000 acts as a bonding agent. The average hardness of the tablet was about 4-6 kP, and the disintegration time was less than 60 seconds.

Example 2

Bilayer Tablet Comprising Antihistamine and Decongestant

Orally disintegrating bilayer tablets can be prepared comprising the active agents of many common allergy medications: phenylephrine HCl and brompheniramine maleate. One layer contains phenylephrine; the other layer contains brompheniramine maleate. Both layers are orally disintegrating.

Tablet hardness is about 4-6 kP, and disintegration time (for each layer and for the entire tablet) is less than 60 seconds.

Example 3

Bilayer Tablet Comprising Ibuprofen

Orally disintegrating bilayer tablets can be prepared comprising ibuprofen. Both layers are orally disintegrating. Each layer contains ibuprofen as the active agent, but in different amounts. A first layer contains about 100 mg ibuprofen, and a second layer contains about 300 mg ibuprofen. The ibuprofen is coated with a taste-masking coating and/or enteric coating.

Tablets are compressed on a double rotary 27 station two layer tablet press fitted with forced feeder and pre-compression setup (General Mechanical Industries (GMI)). Tablets are compressed at a force to achieve a hardness of 4 to 6 KP.

The disintegration time is less than sixty seconds.

Example 4

Bilayer Tablet Comprising Aspirin and Pravastatin

Orally disintegrating bilayer tablets can be prepared comprising aspirin and a statin, e.g., pravastatin. One layer contains aspirin; the other layer contains pravastatin. The layers are formulated as follows:

TABLE 3

Layer formulation comprising aspirin

| Component | Amount for 80 mg Tablet | Amount for 325 mg Tablet |
|---|---|---|
| Encapsulated Aspirin | eqv. to 80 mg Aspirin | 80 mg-325 mg |
| Lactose/microcrystalline cellulose/Dextromonohydrate/ Mannitol granules* | qs to make 300 mg tablet layer | qs to make 500 mg tablet layer |
| Polyplasone XL-10 | 3 to 4% | 3 to 4% |
| Tween 80 | 0.2 to 0.4% | 0.2 to 0.4% |
| Cocoa butter | 3 to 4% | 3 to 4% |
| Magnesium Stearate | 0.1%-0.5% | 0.1%-0.5% |
| Talc | 0.1-0.5% | 0.1-0.5% |

*This is an inert granulation for bulking, if necessary. The bulking granulation contains 50%-90% lactose anhydrous, 10%-50% microcrystalline cellulose, 40% to 70% Dextrose monohydrate, 45% to 75% Mannitol granules and 0.1%-0.5% zinc stearate. The ingredients are blended, and appropriate size granules are prepared by conventional dry granulation process. Alternative excipients can be used to prepare inert granules for bulking by dry or wet granulation processes. The granules do not have an alkalizing agent, do not contain excessive moisture, and are compatible with the active agent granules. The bulking granulation allows compression of bilayer tablets.

The aspirin granulation is blended with a quantity of the bulking granulation to achieve a bulk amount sufficient to compress a satisfactory layer. The aspirin granules and bulking granules are blended with zinc stearate or high melting point hydrogenated powdered waxes as lubricants.

TABLE 4

Layer formulation comprising pravastatin

| Component | Amount (% weight/weight) |
|---|---|
| Pravastatin | 20 mg-40 mg |
| Calcium Carbonate | 50 mg-250 mg |
| PEG 8000 | |
| Magnesium Oxide | 50 mg-100 mg |
| Magnesium Carbonate | 25 mg-50 mg |
| Cocoa butter | 3 to 4% |
| Corn Starch | 25 mg-50 mg |
| Magnesium stearate | 0.2%-0.5% |

The ingredients of the pravastatin layer formulation are wet granulated using starch paste or other wet granulating materials, e.g., PVP or HPMC. Alternatively, the pravastatin layer can be dry granulated by compaction. The granules can be sized and lubricated.

In this embodiment, cocoa butter acts as a bonding agent in the aspirin layer, and PEG 8000 acts as a bonding agents in the statin layer.

The two tablet layers are compressed using appropriate conventional tools and a suitable bilayer tabletting press to form the bilayer tablet.

The bilayer tablets can be coated with an HPMC dispersion and/or with a colored coating. Coating can be performed by any conventional coating equipment and techniques. The coating is applied to a thickness of about 0.2%-2% or to any desired level (based on the weight of the finished coated bilayer tablet).

Example 5

Bilayer Tablet Comprising Enteric-Coated Aspirin and a Statin

Orally disintegrating bilayer tablets can be prepared according the preceding example, but containing enteric-coated aspirin and a statin (e.g., simvastatin, lovastatin, or cerivastatin). Enteric-coated aspirin granules can be purchased commercially or can be prepared by generally known procedures.

Example 6

In Vivo Disintegration

The orally disintegrating compositions can be evaluated for in vivo disintegration time. Subjects are asked to record the time for the tablet to partially and/or completely disintegrate in the mouth. Data from multiple subjects can be summarized and analyzed.

Example 7

In Vitro Disintegration

An in vitro disintegration test can be performed according to USP 29, <701> Disintegration, pp. 2670-2672. Many embodiments of the present invention exhibit an in vitro disintegration time of less than 45 seconds.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

It is further to be understood that all values are approximate, and are provided for description.

Patents, patent applications, publications, product descriptions, and protocols cited throughout this application are incorporated herein by reference in their entireties for all purposes.

What is claimed is:

1. A tablet composition comprising at least two layers, wherein
 a. at least one layer comprises an active agent;
 b. the at least two layers each independently disintegrate in less than about 60 seconds upon introduction into an oral and/or buccal cavity;
 c. the composition comprises a bonding agent, where the bonding agent is a fat or a wax having a melting point of about 25° C. to about 90° C.; polyethylene glycol 8000; or a polyethylene glycol ester, wherein the bonding agent maintains cohesion between the at least two layers;
wherein each layer comprises at least one bonding agent; and
wherein, upon introduction into the oral and/or buccal cavity, at least two layers of the composition are simultaneously in contact with said cavity.

2. The composition of claim 1, wherein the fat is cocoa butter, hydrogenated tallow, hydrogenated vegetable oil, hydrogenated cotton seed oil, hydrogenated palm kernel oil, soybean oil, stannol ester, or derivatives or mixtures thereof.

3. The composition of claim 1, wherein the bonding agent is present in an amount of about 0.01% to about 5% by weight of the layer.

4. The composition of claim 1, further comprising a means for increasing disintegration, wherein the means for increasing disintegration is one or more super-disintegrants, salivating agents or combinations thereof.

5. The composition of claim 4, wherein the means for disintegration is one or more salivating agents selected from the group consisting of a super-emulsifier and a food acid.

6. The composition of claim 5, wherein the means for disintegration is one or more super-emulsifiers selected from the group consisting of: alkyl aryl sulfonates, alkyl sulfates, sulfonated amides and amines, sulfated and sulfonated esters and ethers, alkyl sulfonates, polyethoxylated esters, mono- and diglycerides, diacetyl tartaric esters of monoglycerides, polyglycerol esters, sorbitan esters and ethoxylates, lactylated esters, phospholipids, lecithin, polyoxyethylene sorbitan esters, propylene glycol esters, and sucrose esters or combinations thereof.

7. The composition of claim 5, wherein the means for disintegration is one or more food acids selected from the group consisting of: citric acid, malic acid, tartaric acid, salts thereof or combinations thereof.

8. The composition of claim 4, wherein the means for disintegration is one or more salivating agents present in an amount of about 0.05% to about 15% by weight of the layer.

9. The composition of claim 1, wherein the composition remains substantially intact upon friability testing.

10. The composition of claim 9, wherein the composition is a bilayer tablet.

11. The composition of claim 10, wherein both layers of the bilayer tablet are capable of oral disintegration in less than 45 seconds.

12. The composition of claim 10, wherein the bilayer tablet comprises:
 a. a first layer that is capable of oral disintegration in less than 45 seconds; and
 b. a second layer that is not capable of oral disintegration in less than 45 seconds.

13. The composition of claim 9, wherein the composition comprises at least one layer that does not contain an active agent.

14. The composition of claim 9, wherein the composition is formed into a dosage form by compression.

15. The composition of claim 9, wherein the composition further comprises a coating, wherein the coating is a barrier coating.

16. The composition of claim 9, wherein at least one layer comprises a super-disintegrant.

17. The composition of claim 9, wherein at least one layer comprises a super-emulsifier.

18. The composition of claim 1, wherein the composition is made by a process comprising compressing said at least two layers together with a tabletting press to produce a composition where the first layer and the second layer are adjacent to one another.

19. The composition of claim 1, wherein the hardness of the composition is about 4 to about 7 kP.

20. The composition of claim 1, wherein the friability, when tested according to USP 29, <1216> is less than 1% loss.

21. The composition of claim 1, wherein the bonding agent maintains cohesion between the at least two layers thereby maintaining tablet integrity such that the at least two layers remain attached to one another during friability testing, storage, transport, and/or handling.

22. The composition of claim 5, wherein the means for disintegration is one or more food salts, sodium chloride, salt substitutes, and potassium chloride or combinations thereof.

23. A composition for oral administration comprising at least two layers, wherein
 a. at least one layer comprises an active agent;
 b. the at least two layers each independently disintegrate in less than about 60 seconds upon introduction into an oral and/or buccal cavity; and
 c. the composition comprises a means for maintaining layer cohesion, wherein said means melts in response to tabletting compression forces and, after said melting, maintains interlayer cohesion such that the at least two layers remain attached to one another during friability testing, storage, transport, and/or handling,
 wherein, upon introduction into the oral and/or buccal cavity, at least two layers of the composition are simultaneously in contact with said cavity.

24. The composition of claim 23, wherein the means for maintaining layer cohesion is a fat or wax.

25. The composition of claim 24, wherein said means for maintaining layer cohesion comprises cocoa butter, hydrogenated tallow, hydrogenated vegetable oil, hydrogenated cotton seed oil, hydrogenated palm kernel oil, soybean oil, stannol ester, or a derivative thereof.

26. The composition of claim 23, wherein the means for maintaining layer cohesion is polyethylene glycol 8000, a polyethylene glycol ester or mixtures thereof.

27. The composition of claim 23, wherein the means for maintaining layer cohesion is present in an amount of about 0.01% to about 5% by weight of the layer.

* * * * *